(12) United States Patent
Calvani

(10) Patent No.: US 7,833,977 B2
(45) Date of Patent: Nov. 16, 2010

(54) USE OF L-CARNITINE AS STABILIZING AGENT OF PROTEINS

(75) Inventor: Menotti Calvani, Pomezia (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 670 days.

(21) Appl. No.: 10/470,999

(22) PCT Filed: Dec. 15, 2000

(86) PCT No.: PCT/IT00/00520

§ 371 (c)(1), (2), (4) Date: Dec. 1, 2003

(87) PCT Pub. No.: WO02/48190

PCT Pub. Date: Jun. 20, 2002

(65) Prior Publication Data

US 2004/0120967 A1   Jun. 24, 2004

(51) Int. Cl.
*A61K 38/00* (2006.01)

(52) U.S. Cl. ....................................................... 514/12
(58) Field of Classification Search .................... 514/12
See application file for complete search history.

(56) References Cited

U.S. PATENT DOCUMENTS

| 5,037,851 A * | 8/1991 | Cavazza ..................... 514/556 |
| 2003/0068309 A1 | 4/2003 | De Simone |
| 2004/0058015 A1 | 3/2004 | Tao |
| 2004/0120967 A1 | 6/2004 | Calvani |
| 2004/0142879 A1 | 7/2004 | Calvani |
| 2005/0118153 A1 | 6/2005 | Simone |
| 2005/0163873 A1 | 7/2005 | Ritch |
| 2005/0186196 A1 | 8/2005 | De Simone |
| 2005/0197280 A1 | 9/2005 | De Simone |
| 2006/0004095 A1 | 1/2006 | Calvani et al. |
| 2006/0241058 A1 | 10/2006 | Amato et al. |

OTHER PUBLICATIONS

Peluso et al. (J. Cellular Biochemistry 2000; 80: 1-10).*
Strauss et al. (J. Mol. Cell Cardiol. 1998; 30: 2319-2325).*
Swamy-Mruthinti et al. (Exp. Eye. Res. 1999; 69: 109-115).*
Cobb et al. (Biochemistry 2002; 41: 483-490).*
Horwitz (Proc. Natl. Acad. Sci. 1992; 89: 10449-10453).*
Snoeckx et al. (Physiological Reviews 2001; 81: 1461-2325).*
Oimomi et al. (Exp. Eye. Res. 1988; 46: 415-420).*
Malina et al. (BMC Opthalmology 2002; 2; 1).*
Swamy-Mruthinti et al. (Exp. Eye. Res. 1999; 69: 109-115).*
Swamy-Mruthinti et al. (Exp. Eye. Res. 1999; 69: 109-115).*
Horwitz (PNAS 1992; 89: 10449-10453).*
Swamy-Mruthinti et al, "Inhibition of glycation and glycation mediated changes by L-carnitine in diabetic rat lenses", FASEB Journal, vol, 14, No. 4, Mar. 15, 2000, p. A504.
Peluso et al, "Carnitine: An Osmolyte That Plays a Metabolic Role", Journal of Cellular Biochemistry, vol. 80, No. 1, 2000, pp. 1-10.
Swamy-Mruthinti et al, Acetyl-L-Carnitine Decreases Glycation of Lens Proteins: in vitro Studies, Experimental Eye Research, vol. 69, No. 1, Jul. 1999, pp. 1009-1115.

* cited by examiner

*Primary Examiner*—Brandon J Fetterolf
(74) *Attorney, Agent, or Firm*—Lucas & Mercanti, LLP

(57) ABSTRACT

The present invention relates to the technical field of stabilizing proteins, in particular to the therapeutic aspects of protein stabilization. L-carnitine is a useful agent for stabilizing proteins, and in a particularly favourable aspect in proteins used in the medical field. In a preferred aspect, L-carnitine is used for protecting chaperone activity, and in the medical field for preserving the activity of altered chaperone proteins. In connection with this invention L-carnitine is used for the preparation of a medicament for the treatment of diseases due to altered chaperone proteins, such as eye diseases, in particular cataract.

12 Claims, No Drawings

USE OF L-CARNITINE AS STABILIZING AGENT OF PROTEINS

This application is the US national phase of international application PCT/IT00/00520 filed 15 Dec. 2000 which designated the U.S.

The present invention relates to the technical field of stabilizing proteins, in particular to the therapeutic aspects of protein stabilization.

BACKGROUND OF THE INVENTION

In the production of proteins and polypeptides, either by extraction or by recombinant biotechnology techniques, there is the problem of maintaining the correct folding of the protein so as to keep its desired activity.

Unfolding or incorrect or otherwise modified foldings may occur because of technical manipulation or the general processing system for the production of the proteins.

Another problem in proteinaceus material processing is given by the aggregation of proteins.

Many solutions are offered in the state of the art. Some of them are peculiarly chemical, meaning by this that chemical reagents are used, such as, for example particular mixtures of salts, even in buffer solutions.

U.S. Pat. No. 5,728,804, to research Corporation Technologies, discloses a method for protein renaturation by means of detergent-free cyclodextrins. U.S. Pat. No. 5,563,057, to Wisconsin Alumni Research Foundation, other than cyclodextrin, teaches the use of certain detergents for refolding misfolded enzymes.

U.S. Pat. No. 5,874,075, to Amgen, discloses protein:phospholipids complexes useful for stabilizing proteins against thermally-induced aggregation, denaturation and loss of activity.

U.S. Pat. No. 5,756,672, to Genentech, provides a composition comprising a polypeptide in a certain buffer. Said buffer being suitable for refolding improperly folded polypeptides. A particular embodiment is given for refolding misfolded insulin-like growth factor-I.

The above mentioned methods might be convenient, since easily available chemicals are used, but may raise some instances for certain chemicals used, for example copper or manganese salts (U.S. Pat. No. 5,756,672).

Refolding occurs also through chromatographic techniques, See Altamirano M M. Et al. *Nat. Biotechnol.* 1999 February; 17(2):187-91.

The discovery of chaperonins has opened a new field for the technology of protein processing.

Chaperonins, also known as heat-shock proteins or HSP; are natural proteins exerting a biological role in protein folding. See for an extensive review internet address ermm.cbcu.cam.ac.uk/000021015h.htm by Julia C. Ranford, Anthony R. M. Coates and Brian Handerson.

Technically, chaperonins are intensively studied as means for facing the above-mentioned problem of protein stabilization and refolding.

This search leads to newly discovered chaperonins and to their use for protein stabilization, see for example U.S. Pat. No. 5,428,131, to Yale University. For a picture of chaperonins for the technical problem faced by the present invention, see for example U.S. Pat. No. 5,688,651, to RAMOT University; U.S. Pat. No. 5,646,249, to U.S. Health Department; U.S. Pat. No. 5,561,221, to Nippon Oil Company Limited, WO 00/20606, to Reiman and Schirmbeck, J P 11266865, to Kaiyo Biotechnology Kenkyusho K K, WO 99/40435, to Netzer; JP 10327869, to Kaiyo Biotechnology Kenkyusho K K; WO 00/71723, to Roche Diagnostics; WO 00/55183 and WO 99/05163, to Medical Research Council.

Chaperonins are a useful tool for protein stabilization and refolding, but some technical drawbacks come from their use. Since they are proteins, even they are prone to alteration, such as thermal one, so they too need some protective factor.

For the technical field of stabilizing proteins, this problem is also very important for preparation of HSP cancer vaccines. It has been observed that the immunogenicity of a given antigen is rendered far more efficient when it is presented to immune cells in a complex with HSPs (Requena J M et al, Ars-Pharm 1997, 38(2-3):191-208; Castellino F, et al, J Exp Med 2000, 191(11):1957-1964). Particularly, the immune response to cancer is boosted with HSP (i.e., HSP70 or gp96) which are linked to an antigenic peptide ("specific antigenic fingerprints"), both of which are obtained from the patient's cancer cells (Yedavelli Spet al Int J Mol Med 1999, 4(3):243-248). It is therefore important to have stable and/or well preserved HSP for cancer vaccines.

Interestingly, some chaperoning, such as the eye lens alpha-crystallin proteins, are members of the small heat shock protein (sHSP) family. sHSPs have been shown to function in a number of different processes ranging from RNA stabilization to elastase inhibition and interaction with the cytoskeleton.

AlphaA-crystallin is localized primarily in the lens with very low levels found in other tissues, whereas alphaB-crystallin is now known to be essentially ubiquitous throughout the body (Haley D A et al, J Mol Biol 1998, 277:27-35). The biological importance of alphaB-crystallin is highlighted by its elevated levels in ischemic heart and in the brains of patients with multiple sclerosis, Alzheimer's and other neurological diseases. Consistent with its classification as an HSP, expression of alphaB-crystallin has been shown to be induced by a variety of physiological stresses including heat, osmotic stress, and metal toxicity. The biological importance of alphaA-crystallin in lens is highlighted by its efficient suppression of uncontrolled aggregation of damaged proteins.

As it appears from the above examples, the stabilization of chaperoning, either for their use or for stabilizing them in those pathological states in which their are altered, is very important in the medical field.

ABSTRACT OF THE INVENTION

It has now been found that L-carnitine has a surprising effect in stabilizing proteins, and in a particularly favourable aspect for the medical field, L-carnitine has a surprising effect in protecting chaperone activity, this protecting activity being exerted through a stabilizing effect by L-carnitine toward chaperone activity.

Therefore, it is an object of the present invention the use of L-carnitine or of a salt thereof for stabilizing proteins, in particular as auxiliary factor in protecting chaperone activity.

In one preferred embodiment of the present invention, L-carnitine is used in the therapeutical field, for preserving the activity of altered chaperone proteins.

In connection with the first preferred embodiment, L-carnitine is used for the preparation of a medicament for the treatment of diseases due to altered chaperone proteins.

In a second preferred embodiment of the present invention, L-carnitine is used for the preparation of a medicament for the treatment of diseases based on altered activity of alpha-crystallin protein, more particularly AlphaA- and/or alphaB-crystallin. Diseases that may be treated are for example ischemic heart and in the brains of patients with multiple sclerosis, Alzheimer's and other neurological diseases. In a third preferred embodiment, the disease is an ophthalmic affection where α-crystallin is the altered chaperone protein. In a particular aspect, the present invention applies in the treatment of cataract, excluding cataract of diabetic origin.

Proteins, in particular chaperonines, such as HSP, stabilized by means of L-carnitine are also an object of the present invention.

Accordingly, further objects of the present invention are the use of L-carnitine or a pharmaceutically salt thereof for the manufacture of a medicament for the treatment of cataract of non-diabetic origin.

A particular object of the present invention is an ophthalmic composition comprising a suitable amount of L-carnitine or a pharmaceutically salt thereof. This ophthalmic composition can optionally comprise a further active ingredient useful for the treatment of cataract of non-diabetic origin.

The above objects of the present invention shall be illustrated in detail also by means of examples.

DETAILED DESCRIPTION OF THE INVENTION

For pharmaceutically acceptable salt of L-carnitine, it is intended any salt, organic and inorganic suitable for use in medical field, human and veterinary. In the general field of protein stabilization, any salt may be used, with the condition that it is compatible with the specific application.

Examples of pharmacologically acceptable salts of L-carnitine, though not exclusively these, are chloride; bromide; iodide; aspartate; acid aspartate; citrate; acid citrate; tartrate; acid tartrate; phosphate; acid phosphate; fumarate; acid fumarate; glycerophosphate; glucose phosphate; lactate; maleate; acid maleate; mucate; orotate, oxalate; acid oxalate; sulphate; acid sulphate; trichloroacetate; trifluoroacetate; methane sulphonate; pamoate and acid pamoate.

DETAILED DESCRIPTION OF THE PREFERRED EMBODIMENT

The ocular lens is a transparent organ constituted by a highly concentrated and highly ordered matrix of structural proteins, called 'crystallins', which are probably the longest lived proteins of the body (Wistow, G., and Piatigorsky, J. (1988), Ann. Rev. Biochem, 57, 479-504; Blomendal, H: (1982) Biochem. 12, 1-38; Bettelheim, F. A. (1985) The Ocular Lens. Structure, Function, and Pathology, (Maisel H. ed.) pp. 265-300, Marcel Dekker, Inc, New York; Tardieu, A., and Delay, M. (1988), Ann. Rev. Biophys. Chem. 17, 47-70).

Post-translational modifications of lens crystallin, consequent to aging or diseases such as diabetes, may result in conformational changes and aggregation of these proteins, and lead to lens opacification and cataract formation (Harding, D. (1981), Molecular and Cellular Biology of the Eye Lens (Bloemendal H., ed) pp. 327-365, John Wiley and Sons, New York). Although the mechanisms of cataractogenesis are not well understood, oxidation of lens proteins is associated with cataract in mammals (Francis, P. J. (1999), Trends in Genetics 15, 191-196).

The lens undergoes major oxidative stress because it is constantly exposed to light and oxidants (Varma, S. D., et al. (1984), Curr Eye Res 3, 35-57, Spector, A. (1995), FASEB J. 9, 1173-1182; Taylor, A., and Davies, K J. (1987), Free Radic Biol Med 3, 371-377; Zigman, S. (1981), Mechanisms of Cataract Formation in the Human Lens (Ducan G, ed.) pp. 117-149, Academic press, New York; I. Dillon, J. (1985), The Ocular Lens. Structure, function, and Pathology, Maisel H. ed, Marcel Dekker, Inc., New York, 349-366 Zigman, S. (1985), The Ocular Lens. Structure, Function and Pathology. (Maisel H. ed.) pp. 301-347 Marcel Dekker, Inc., New York). Oxidative modifications include selective oxidation of specific amino acids that results in charge alterations, protein degradation, protein cross-linking and insolubilization, and increased non-tryptophan fluorescence (Spector, A., and Garner, W. H. (1981), Exp Eye Res. 33, 673-681 Andley, U. P. (1987), Photochem. Photobiol. 46, 1057-1066 Davies, K. J. A., et al (1987), J Biol Chem. 262, 9914-9920 Augusteyn, R. C. (1981), Mechanisms of Cataract Formation in the Human Lens (Ducan, G., ed.) pp. 72-115, Academic Press, London Zigler, J. S. Jr et al (1989), Free Radic Biol Med. 7, 499-505). Consequently, the lens has developed antioxidant systems and repair mechanisms to counteract the effect of oxidants. The first line of defense against oxidation stress is constituted by radical scavenging antioxidants that reduce the oxidative insult. For example, glutathione (GSH) and taurine, which are both highly represented in lens tissue, exert protective effects in an in vitro model of diabetic cataract (Richard R C Et al (1998), Proc Soc Exp Biol Med 217, 3 97-407 Jones, R. A. V. and Hothersall, J. S. (1999), Exp Eye Res. 69, 291-300). Furthermore, α-crystallin, which constitutes up to 50% of the total protein mass of the mammalian lens, acts as a molecular chaperone that prevents heat-induced aggregation of numerous proteins and is required for the renaturation of chemically denaturated proteins (Jones, R. A. V. and Hothersall, J. S. (1999), Exp Eye Res. 69, 291-300). A key element of α-crystallin function is its ability to prevent aberrant protein associations by binding to transiently exposed hydrophobic protein surfaces (van den Ussel P. R. et al. (1996), Ophthalmic Res. 28, 39-43). Because α-crystallin prevents both ultraviolet radiation- and free radical-induced aggregation of proteins in vitro (Groenen P J et al (1994) Eur. J Biochem. 225, 1-19 Andley, U. P. et al (1998) J Biol Chem. 273, 31252-31261; Lee, J. S. et al (1997) J Protein Chem. 16, 283-289; Kramps, J. A. Et al (1978), Biochem Biophys Acta 533, 487-495; Van Kleef, F. S. M., et al (1976), Eur J Biochem 66, 477-483 Smulders, R. H. P. H. et al (1996), J Biol Chem 271, 29060-29066.), it may also protect lens proteins from photooxidative changes in vivo.

U.S. Pat. No. 5,037,851, issued on Aug. 6, 1991, with a priority claim of Nov. 15, 1988, in the name of the same assignee of the present invention, claims a therapeutic method for the treatment of cataract which comprises administering orally or parenterally to a subject having a cataract 1000 to 2000 mg/day of acetyl D-carnitine or an equivalent quantity of one of its pharmacologically acceptable salts. The teaching of this patent is limited to acetyl D-carnitine.

The present inventor and colleagues previously showed that in experimental animal diabetes the decrease in lens carnitine, a ubiquitous molecule involved in many biological pathways, is an early important and selective event possibly related to cataract formation (Pessotto P, et al. (1997) Exp. Eye Res. 64, 195-201). In this paper, there is disclosed how in the diabetic states there is a loss of L-carnitine in the lens and the carnitine levels in the other eye tissues seem substantially unaffected. The authors conclude that the role of L-carnitine in lens is still unclear, but its loss may be related to the appearance of cataract. There is a strong suggestion in this reference to use acetyl carnitine, giving a good reason for expectation of success, for the prevention of the appearance of cataract by a pharmacological action, as has been shown for aspirin. The reason for an expectation of a favourable action by acetyl carnitine, in view of the well-known action of aspirin, is that both compounds have acetylating properties, which, on their turn are responsible for the protection of lens proteins.

In addition to its primary function as a carrier of long-chain fatty acids from the cytoplasm to the sites of β-oxidation, it has been anticipated that L-carnitine could also serve to maintain cell homeostasis.

Swamy-Mruthinti, S., and Carter, A. L. (1999), Exp Eye Res 69, 109-115 demonstrate that L-carnitine results ineffective in in vitro glycation of lens crystallins, while acetyl L-carnitine and acetyl salicylic acid decreased crystallin glycation. These considerations explain why L-carnitine levels in various animal tissues do not invariably correlate with tissue energy requirements or with lipid metabolism. For example, the eye lens, a non-vascularized tissue whose main source of energy is glucose absorbed from ocular fluids, has higher L-carnitine concentrations than other eye compartments (Pessotto, P. et al (1994) J Ocul. Pharmacol. 10, 643-651).

1. This invention accordingly contemplates the use of L-carnitine and its pharmacologically acceptable salts to produce an ophthalmic pharmaceutical composition for the therapeutic treatment of cataract, in particular cataract of non-diabetic origin. In practice, a therapeutically effective amount of L-carnitine or an equivalent quantity of one of its pharmacologically acceptable salts is administered to the eye, optionally comprising a further active ingredient useful for the treatment of cataract of non diabetic origin.

Preferably, the composition is in the form of a collyrium. The collyrium is applied to the extent of the therapeutic necessity, as determined by the skilled person and depending on the conditions of the patient, the severity of the illness and any other factor considered by the skilled person. For example, 2-3 drops 3-4 times daily may be suitable.

The compositions for the collyrium comprise the usual sterile isotonic solution. The choice of the suitable excipients is within the capabilities of a normally skilled person in pharmaceutical technology. For example, use is made of excipients such as sodium chloride, dibasic sodium phosphate, monobasic potassium phosphate, benzalkonium chloride, and ethyl alcohol. The composition is brought to the correct volume with distilled water.

EXAMPLE

Materials and Methods

Lens Organ Culture

Four-month-old Sprague-Dawley rats were anesthesized with 5 mg/kg xylazine and 65 mg/kg ketamine, and decapitated. Immediately after, eyes were enucleated, extracted and placed in 2 ml of modified TC-199 medium. Lens integrity was assessed by measuring protein leached into the medium after 30-60 min of culture; damaged lenses were discarded. One lens of each pair was placed in culture medium with no $H_2O_2$ and used as a control. After 24 h of culture, the control lenses did not differ from freshly enucleated lenses in any of the parameters evaluated in this study. The controlateral lens of each pair was placed in medium and, after equilibration under 5% $CO_2$ at 37° C., was exposed to 500 μM $H_2O_2$ in the absence or presence of 300 μM L-carnitine. After 24 h of incubation, morphological characteristics and changes were recorded, and the lenses were photographed. The incubated lenses were rinsed with saline solution, blotted on filter paper, weighed, and then immediately processed for biochemical analysis. To determine lactate dehydrogenase (LDH) leakage, lenses were incubated individually in each different medium, and the medium was harvested daily and saved for LDH analysis.

Extraction of Lens Proteins

Decapsulated lenses were homogenized with disposable pestles and then sonicated in extract buffer (20 mM HEPES, 0.2 mM EDTA, 0.5 mM dithiothreitol, 450 mM NaCl, 25% glycerol, 0.5 μM/ml leupeptin, 0.5 μg/ml protinin, 0.5 mM phenylmethanesulfonyl fluoride) on ice. Aliquots of the homogenate from each of the incubated lenses were removed for GSH and L-carnitine analysis. The remainder was centrifuged for 25 min at 20,000×g to separate the supernatant from the pellet. The pellet was washed with 1.0 ml buffer and dried under nitrogen. This fraction was designated "water-insoluble fraction". The supernatant fraction was dialyzed twice against 3 ml of 0.025 mol/l phosphate buffer, pH 7.4 for 48 h and lyophilized. This fraction was designated "water-soluble" fraction. The water-soluble and water-insoluble fractions were delipidated with 3.0 ml chloroform:methanol (2:1) for 16 h under shaking followed by centrifugation at 2,000 g for 5 min.

After the organic solvent was discarded, the residue was treated with 2.0 ml of diethyl ether, left to stand for 5 min and then centrifuged at 2,000 g for 5 min. The pellet was dried under air and stored at 4° C. in a desiccator.

Preparation of Crystallins

The water-soluble crystallin fractions were isolated by preparative Sephacryl S-300-HR gel permeation chromatography as previously described (Smulders, R. H. P. H. et al (1996), J Biol Chem 271, 29060-29066., de Jong, et al (1974), Eur J Biochem. 48, 271-276). Briefly, soluble protein was applied to a 100×1.5-cm column and developed isocratically with phosphate buffer. The total fractions from control and $H_2O_2$±L-carnitine treated lenses were concentrated by ultrafiltration in a Diaflo apparatus and their purity checked by SDS-PAGE, done according to Laemmli using a Bio-Rad Mini-Protean II System. Protein concentrations were measured with a Bradford protein assay kit (Bio-Rad).

Western Blotting

Total lens homogenate was applied on 4-20% gradient sodium dodecyl sulphate (SDS) gels using. Tricine buffers and then transferred to polyvinylidene difluoride membranes. Western blotting was performed as described elsewhere (Kim, S. Y. et al (1995), J Invest Dermatol 104, 211-217). The concentration of antibodies was 5 μg/ml for primary antibody (anti-γ-glutamyl-ε-lysine isopeptide) and 0.1 μg/ml for secondary antibody. The blot was then developed by enhanced chemiluminescence (Pierce, Milan, Italy). Subsequently, the very high molecular weight bands were cut out, eluted into SDS buffer containing Tricine, freed of SDS by ion pair extraction (Konigsberg, W. H., and Henderson, L. (1983) Proc Natl Acad Sci USA. 80, 2467-2471), and subjected to amino acid analysis.

Measurement of isopeptide cross-links in water-insoluble proteins.

The water-insoluble proteins were suspended in 0.2 M N-ethylmorpholine acetate (pH 8.1). An aliquot (10%) was used to quantitate the amount of total protein. Samples were digested by the sequential addition of proteolytic enzymes (collagenase, pronase, aminopeptidase and carboxypeptidase A, carboxypeptidase B and carboxypeptidase y), directly to the reaction mixture at 37° C. in the presence of 0.02% sodium azide. After enzymatic digestion, the free N-(γ-glutamyl)lysine isopeptide cross-link was resolved by HPLC and quantitated by amino acid analysis (Hohl, D., et al (1991), J Biol Chem. 266, 6626-6636). In a related set of experiments, the isopeptide content of lenses was determined without prior extraction.

Tryptophan Fluorescence

The loss of-protein tryptophan fluorescence, an indicator of tryptophan oxidation, seems to be a marker of crystallin integrity. We therefore measured-tryptophan fluorescence in lens crystallin (Perkin-Elmer 650-40 spectrophotometer) according to a previously described method (Jones, R. H. V., and Hothersall, J. S. (1993), Exp Eye Res 57, 783-790). The excitation wavelength was set to 295 nm, and the fluorescence emission was detected at 330 nm.

Evaluation of the molecular chaperone activity of α-crystallins from control and in vitro-treated rat lenses The following experiments were performed essentially as described elsewhere (Horwitz, J. (1992) Proc Natl Acad Sci USA. 89, 10449-10453). The chaperone-like activity of α-crystallin from control and $H_2O_2$±L-carnitine treated lenses was determined by heat denaturation studies. The extent to which the unmodified or modified α-crystallin preparation protected $β_L$-crystallin (used as the target protein) from heat-induced denaturation and aggregation was assessed as follows: 100 μg or 200 μg of α-crystallin were added to 200 μg of $β_L$-crystallin in a 1.5-ml cuvette and made up to a final volume of 1 ml with 50 mM phosphate buffer, pH 7.0. The cuvette was placed in a temperature-regulated cell holder attached to a UV spectrophotometer. Light scattering due to protein denaturation and aggregation was monitored at. 360 nm absorbance for 3,000 s at 55° C. or for 1,800 s at 58° C.

Intermediate filament assembly and viscosity assays involving α-crystallins

The sedimentation assay devised by Nicholl and Quinlan (Nicholl, I. D., and Quinlan, R. A. (1994), EMBO J 13, 945-953) was used to assess α-crystallin-induced inhibition of intermediate filament assembly. Purified porcine glial fibrillary acidic: protein (GFAP) was used for these studies; it was purified from porcine spinal cord by axonal flotation as described previously (Pemg, M. D., et al (1999), J Cell Sci. 112, 2099-2112, MacLean-Fletcher, S., and Pollard, T. D. (1980), Biochem Biophys Res Commun 96, 18-27). The gel formation assay was based on a method used to monitor actin binding protein activity by falling ball viscometry (Pemg, M. D., et al (1999), J Cell Sci. 112, 2099-2112). α-Crystallins were mixed with GFAP in 8 M urea, 20 mM Tris-HCI, pH 8.0, 5 mM EDTA, 25 mM 2-mercaptoethanol and then stepwise dialyzed in 10 mM Tris-HCI, pH 8.0, 25 mM 2-mercaptoethanol. Assembly of the GFAP intermediate filaments, in the presence or absence of α-crystallin, was induced by the addition of a 20-fold concentrated buffer to give a final concentration of 100 mM imidazole-HCI, pH 6.8, 0.5 mM DTT. A 100-μl aliquot of sample was loaded into a glass tube and used for the viscosity assay. The tube was then immersed in a 37° C. water bath for 1 h before the gel formation assay. A ball was then placed into the tube, and the ability of the solution to support the ball was monitored.

Lens Microscopic Examination

After a 24-h incubation with or without $H_2O_2$ in the presence or absence of L-carnitine, lenses were submitted to standard procedures for histologic analysis. For optical microscopy, lenses were removed from culture medium, immersed in fixative (neutral buffered formalin), dehydrated in ethanol, cleared in xylene, and embedded in paraffin wax for sectioning. Five micrometer sections were prepared and stained with hematoxylin and eosin. For scansion electron microscopy the lenses were fixed by immersion, for at least 24 h at room temperature, in a solution of 2.5% glutaraldehyde and 6% sucrose, buffered to pH 7.2 with 50 mM sodium cacodylate. Samples were dehydrated through a graded series of ethanol, critical point-dried using $CO_2$, mounted on aluminium stubs, sputter-coated with gold, and examined with a Leica Stereoscan 440 microscope at a 3-7 kV acceleration voltage.

For transmission electron microscopy, the lenses were fixed as described above for the scansion electron microscopy procedure, postfixed in $OsO_4$ buffered with 150 mM sodium-potassium phosphate (pH 7.4), embedded, sectioned, and stained for electron microscopy. They were examined at a JEOL 100B electron microscope.

Results

Changes in Lens Morphology

After 24 h of incubation, the lenses incubated without $H_2O_2$ (control lenses) retained their clarity, but those exposed to 500 mM $H_2O_2$ became uniformly cloudy throughout the outer cortical region and were swollen (data not shown). As shown in Table 1, at the end of incubation, $H_2O_2$-treated lenses were significantly heavier than control lenses (47±0.2 mg vs 25±0.1 mg). There were no differences in weight between control lenses and lenses treated with both L-carnitine and $H_2O_2$. The lenses treated with $H_2O_2$ alone became opaque, whereas lenses treated with L-carnitine and $H_2O_2$ remained clear. Optical and electron microscopy showed that cell shape was unaltered and that fiber cells were intact in control lenses and in lenses treated with L-carnitine and $H_2O_2$. Ballooning, liquefaction and various degrees of fiber swelling were observed in lenses exposed to $H_2O_2$ alone.

L-carnitine and GSH concentrations in control and $H_2O_2$-treated lenses

Under our experimental conditions, there was no significant difference in GSH and L-carnitine concentrations in control lenses, whereas treatment with 500 mM $H_2O_2$ caused a precipitous drop in GSH and L-carnitine levels (Table 1). The addition of L-carnitine (300 mM) to the lens incubation medium before $H_2O_2$ treatment did not prevent the loss of GSH, but maintained the carnitine concentration almost at the level found in control lenses. To determine whether the decrease of GSH and L-carnitine was related to lens damage, we measured leakage of LDH into the medium. As expected, after $H_2O_2$ treatment the decrease in GSH and L-carnitine levels was accompanied by a significant increase of LDH in the supernatants, indicating that depletion of these factors was indeed associated with lens damage. To determine the protective, effect of L-carnitine, we incubated lenses in culture medium containing 300 mM of the molecule. As expected, the concentration of GSH in lenses treated with L-carnitine and $H_2O_2$ decreased to about the same level as in lenses exposed to $H_2O_2$ alone, but the concentration of LDH in the medium from the lens treated with L-carnitine and $H_2O_2$ was similar to that observed in control lenses. This indicates that L-carnitine can withstand this concentration of $H_2O_2$.

Recovery of high molecular weight proteins in the water-insoluble lens fractions containing isopeptide cross-links.

Water-insoluble proteins constituted only 5% of total proteins in control lenses, but increased to 41% of total proteins in $H_2O_2$-treated lenses (Table 1). The concentrations of water-insoluble proteins in lenses treated with L-carnitine and $H_2O_2$ were the same as those observed in control lenses.

Chaperone-like Function of α-crystallin

The chaperone properties of the purified water-soluble α-crystallin were determined by crystallin (target protein) aggregation assay. Characteristically, $β_L$-crystallin aggregates at elevated temperatures. The addition of α-crystallin either prevents or decreases the heat-induced aggregation of $\beta_L$-crystallin, which is measured by light scattering at 360 nm. Since the ratio of α to β determines the degree of protection against heat-induced aggregation, we used 100 μg or 200 μg of α-crystallin and 200 μg of $\beta_L$-crystallin. As expected, α-crystallin from control lenses exerted chaperone activity. After—incubation with $H_2O_2$, there was a significant decrease in the capacity of —α-crystallin to prevent the heat-induced aggregation of $\beta_L$-crystallin, whereas the presence of L-carnitine in the lens incubation mixture prevented this negative effect.

Gel Forming Assay

Since intermediate filaments such as GFAP are a physiological target of α-crystallins, we tested α-crystallin chaperone activity using falling ball viscosimetry in the gel forming assay (MacLean-Fletcher, S., and Pollard, T. D. (1980), Biochem Biophys Res Commun 96, 18-27).

GFAP is an appropriate target because of the property of α-crystallin to disaggregate GFAP cytoplasmic inclusions. In the absence of α-crystallin, GFAP forms a protein gel that supports the ball used in the viscosity test. To determine whether $H_2O_2$ treatment affected the capacity of lens α-crystallin to disrupt the GFAP network, α-crystallin from control or from $H_2O_2$±L-carnitine-treated lens was added to the gel forming assay. α-Crystallin from control lenses completely inhibited the formation and maintenance of the GFAP gel in the viscosity assay, whereas α-crystallin from lenses treated with $H_2O_2$ alone did not affect gel formation. In addition, α-crystallin from lenses treated with both L-carnitine and $H_2O_2$ blocked GFAP gel formation to the same extent as α-crystallin from control lenses.

Tryptophan Fluorescence Measurements

Tryptophan fluorescence was measured in α-crystallin fractions from control and treated lenses to identify conformational changes. In α-crystallin from $H_2O_2$-treated lenses there was a 2.7-fold loss of tryptophan fluorescence; again, L-carnitine restored the basal value.

Lenses exposed to L-carnitine and oxidative stress remained transparent. Although the present inventors do not wish to be bound to any theory, the protective effect of L-carnitine is not easily explained because L-carnitine per se is not known to exert antioxidant activity (Arduini, A. et al (1992), J Biol Chem. 267, 12673-81). Neither did L-carnitine rescue GSH depletion, which means that the beneficial effect was not mediated by an increase of GSH through, for example, an anaplerotic effect on NADPH, a cofactor of the glutathione reductase enzyme (Pemg, M. D., (1999), J Biol. Chem 47, 3323 5-33243. Wuensch, S. A., and Ray, P. D. (1997), Comp Biochem Physiol B Biochem Mol Biol 118, 599-605). Rather, the fact that LDH leakage into the medium, was not increased in lens treated with L-carnitine and exposed to oxidative stress indicates that the molecule can sustain lens integrity. Here we show that lens α-crystallin chaperone activity is diminished by in vitro oxidative stress, and provide support for the proposal that lens proteins subjected to oxidative insult sustain a high degree of post-translational modifications (Cherian, M., and Abraham, E. C. (1995), Biochem Biophys Res Commun. 212, 184-189). L-carnitine not only reduced the increased post-translational modifications of lens proteins but also afforded significant protection against the decreased chaperone activity of α-crystallin. α-Crystallin has been shown to suppress aggregation of denatured proteins in studies in which mixtures of thermally stressed β-crystallins served as substrate (Kramps, J. A. Et al (1978), Biochem Biophys Acta 533, 487-495). It has been demonstrated that oxidative stress disrupts α-crystallin chaperone activity, which is crucial for maintenance of lens transparency (Zigler, J. S. Jr et al (1989), Free Radic Biol Med. 7, 499-505; Richard R C Et al (1998), Proc Soc Exp Biol Med 217, 3 97-407). Therefore, L-carnitine beneficially affects lens transparency by acting directly on α-crystallin.

Both α- and β-crystallins are N-terminally acetylated. Using screening spot-blot analysis combined with mass spectrometry, Takernoto et al. provided evidence that the N-acetylated-terminal methionine of α-crystallin can be oxidized to methionine sulfoxide in vivo (Sims, N. R., et al (2000), Brain Res Mol Brain Res. 77, 176-184). This oxidation of the N-terminal methionine, which is exposed on the outside of the polypeptide, can negatively affect the function of the protein. In addition to NH3-terminal acetylation, the -amino groups of lysine (Lys) residues are subject to acetylation. All seven Lys residues of bovine (α-crystallin react with aspirin, the extent of acetylation varying from 10% for Lys 88, the least reactive, to 60% for Lys 166, the most reactive (Takemoto, L. et al (1992), Curr. Eye Res. 11, 651-655; Rao, G. N. et al (1985), Biochem. Biophys. Res. Commun. 128, 1125-1127). Aspirin inhibits both glycation and carbamoylation as well as aggregation of lens proteins, presumably through acetylation of Lys residues (Hasan, A. et al (1993), Exp Eye Res. 57, 29-35; Cromptonm, Rixon, K. C., and Harding, J. J. (1985), Exp. Eye Res. 40, 297-311; Rao. G. N., and Cotlier, E. (1988) Biochem. Biophys. Res. Commun. 151, 991-996; Huby, R., and Harding, J. J. (1988), Exp Eye Res. 47, 53-59; Ajiboye, R., and Harding D. (1989), Exp Eye Res. 49, 31-41; Blakytin, R., and Harding J. J. (1992), Exp Eye Res. 54, 509-518). Recently, it has been shown that acetyl-L-carnitine inhibits glycation of (α-crystallin, to a greater extent than other crystallins, through acetylation of the potential glycation sites (Groenen, P. J. et al (1993), Biochem J. 295, 399-404). Glycation seems to be more harmful than acetylation because only glycation products are involved in protein cross-linking and in a significant decrease of the α-crystallin chaperone activity (Groenen, P. J. et al (1993), Biochem J. 295, 399-404, Blakytin, R., and Harding J. J. (1992), Exp Eye Res. 54, 509-518).

TABLE 1

Changes of some biochemical parameters in control lenses and in $H_2O_2$ ± L-carnitine-treated lenses.

| | Lens weight (mg) | Water insoluble protein (%) | Glutathione (μmoles/g w-w) | Free carnitine (nmoles/g w-w) | Acetyl carnitine (nmoles/g w-w) | LDH (units/ml conditioned media) | Total carnitine (nmoles/g w-w) |
|---|---|---|---|---|---|---|---|
| Controls | 25 ± 0.1 | 5 ± 1.1 | 4.87 ± 0.23 | 156 ± 3 | 29 ± 1 | ND | 187 ± 5 |
| $H_2O_2$ | 47 ± 0.2* | 41 ± 1.9* | 2.44 ± 0.69* | 27 ± 2* | 6 ± 1* | 53 ± 6 | 36 ± 3* |
| $H_2O_2$ + L-CAR | 27 ± 0.9 | 5 ± 2.0 | 2.71 ± 0.73* | 151 ± 2 | 37 ± 2** | ND | 189 ± 2 |

P < 0.001,
**P < 0.005,
ND: not detectable

The invention claimed is:

1. A method of preserving oxidant-protective activity of alphaA-crystallin comprising contacting L-carnitine or a salt thereof to an alphaA-crystallin such that said alphaA-crystallin remains oxidant protective, wherein said alphaA-crystallin is present in a nondiabetic, human patient.

2. A method of preserving crystalline lens clarity comprising contacting L-carnitine or a salt thereof to said crystalline lens, wherein said crystalline lens is present in a nondiabetic, human patient.

3. The method according to claim 1, wherein L-carnitine is contacted to the alphaA-crystallin.

4. The method according to claim 2, wherein L-carnitine is contacted to said crystalline lens.

5. A method of treating cataract in a nondiabetic, human patient comprising administering an ophthalmic composition comprised of a therapeutically effective amount of L-carnitine or a salt thereof to an eye of said nondiabetic, human patient.

6. The method according to claim 5, wherein the ophthalmic composition is comprised of a therapeutically effective amount of L-carnitine.

7. The method according to claim 5, wherein said treatment preserves molecular chaperone activity of $\alpha$-crystallin.

8. The method according to claim 6, wherein said treatment preserves molecular chaperone activity of $\alpha$-crystallin.

9. The method according to claim 5, wherein said treatment preserves crystalline lens clarity when exposed to oxidative stress.

10. The method according to claim 6, wherein said treatment preserves crystalline lens clarity when exposed to oxidative stress.

11. The method according to claim 7, wherein said treatment preserves crystalline lens clarity when exposed to oxidative stress.

12. The method according to claim 8, wherein said treatment preserves crystalline lens clarity when exposed to oxidative stress.

* * * * *